United States Patent [19]

Sirvio et al.

[11] Patent Number: 5,532,311
[45] Date of Patent: Jul. 2, 1996

[54] PROCESS FOR MODIFYING SURFACES

[75] Inventors: Larry M. Sirvio, Cottage Grove; Barbara C. Swenson, North St. Paul, both of Minn.

[73] Assignee: Minnesota Mining and Manufacturing Company, St. Paul, Minn.

[21] Appl. No.: 381,754

[22] Filed: Feb. 1, 1995

[51] Int. Cl.$^6$ ............................ C08G 63/48; C08G 63/91
[52] U.S. Cl. ........................................ 525/54.2; 525/54.23
[58] Field of Search ........................... 525/54.2, 54.23

[56] References Cited

U.S. PATENT DOCUMENTS

| | | | |
|---|---|---|---|
| 2,016,962 | 10/1935 | Flint et al. | 536/55.3 |
| 2,918,462 | 12/1959 | Druey et al. | 536/55.2 |
| 3,096,602 | 7/1963 | Newmarker, Jr. et al. | 53/22 |
| 3,453,194 | 7/1969 | Bennett et al. | 427/551 |
| 3,475,358 | 10/1969 | Bixler et al. | 523/112 |
| 3,616,935 | 11/1971 | Love et al. | 210/500 |
| 3,617,344 | 11/1971 | Leininger | 117/47 |
| 3,634,123 | 1/1972 | Eriksson et al. | 117/47 |
| 3,639,141 | 2/1972 | Dyck | 117/47 |
| 3,673,612 | 7/1972 | Merrill et al. | 3/1 |
| 3,766,104 | 10/1973 | Bonin et al. | 523/112 |
| 3,796,634 | 3/1974 | Haynes et al. | 195/63 |
| 3,810,781 | 5/1974 | Eriksson et al. | 117/47 |
| 3,826,678 | 7/1974 | Hoffman et al. | 117/81 |
| 3,846,353 | 11/1974 | Grotta | 523/112 |
| 3,853,804 | 12/1274 | Yen et al. | 524/233 |
| 3,947,352 | 3/1976 | Cuatrecasas et al. | 210/31 |
| 4,001,583 | 1/1977 | Barrett | 250/303 |
| 4,046,725 | 9/1977 | Pusineri | 523/112 |
| 4,048,064 | 9/1977 | Clark, III | 210/23 |
| 4,085,019 | 4/1978 | Green | 427/551 |
| 4,102,746 | 7/1978 | Goldberg | 195/63 |
| 4,116,898 | 9/1978 | Dudley et al. | 524/47 |
| 4,118,485 | 10/1978 | Eriksson et al. | 424/183 |
| 4,217,338 | 8/1980 | Quash | 424/1 |
| 4,229,838 | 10/1980 | Mano | 3/14 |
| 4,239,664 | 12/1980 | Teng et al. | 524/47 |
| 4,265,827 | 5/1981 | Sabacky | 524/47 |
| 4,265,927 | 5/1981 | Ericksson et al. | 427/2 |
| 4,268,423 | 5/1981 | Rohrbach et al. | 252/430 |
| 4,301,067 | 11/1981 | Koshugi | 260/112.5 |
| 4,326,532 | 4/1982 | Hammar | 128/349 |
| 4,329,383 | 5/1982 | Joh | 428/36 |
| 4,331,697 | 5/1982 | Kudo et al. | 427/2 |
| 4,349,467 | 9/1982 | Williams et al. | 525/54.2 |
| 4,350,806 | 9/1982 | Wagener | 528/289 |
| 4,424,346 | 1/1984 | Hall et al. | 536/20 |
| 4,521,564 | 6/1985 | Solomon et al. | 525/54.1 |
| 4,526,714 | 7/1985 | Feijen et al. | 260/112 |
| 4,565,740 | 1/1986 | Golander et al. | 428/409 |
| 4,600,652 | 7/1986 | Solomon et al. | 428/423.3 |
| 4,613,517 | 9/1986 | Williams et al. | 427/2 |
| 4,613,665 | 9/1986 | Larm | 536/20 |
| 4,642,242 | 2/1987 | Solomon et al. | 427/2 |
| 4,720,512 | 1/1988 | Hu et al. | 523/112 |
| 4,786,556 | 11/1988 | Hu et al. | 428/412 |
| 4,806,595 | 2/1989 | Noishiki et al. | 525/54.2 |
| 4,810,784 | 3/1989 | Larm | 536/20 |
| 4,865,870 | 9/1989 | Hu et al. | 427/2 |
| 4,876,126 | 10/1989 | Takemura et al. | 428/35.7 |
| 4,944,767 | 7/1990 | Barbucci et al. | 623/66 |
| 4,987,181 | 1/1991 | Bichon et al. | 525/54.1 |
| 5,013,717 | 5/1991 | Solomon et al. | 514/56 |
| 5,047,020 | 9/1991 | Hsu | 604/266 |
| 5,049,403 | 9/1991 | Larm et al. | 427/2 |
| 5,053,048 | 10/1991 | Pinchuk | 623/1 |
| 5,061,750 | 10/1991 | Feijen et al. | 525/54.1 |
| 5,116,962 | 5/1992 | Stuber et al. | 525/54.2 |
| 5,132,108 | 7/1992 | Narayanan et al. | 424/78.17 |
| 5,145,956 | 9/1992 | Lam et al. | 536/124 |
| 5,159,050 | 10/1992 | Onwumere | 528/67 |
| 5,165,919 | 11/1992 | Sasaki et al. | 424/488 |
| 5,182,317 | 1/1993 | Winters et al. | 523/112 |
| 5,198,493 | 3/1993 | Holmberg et al. | 525/54.1 |
| 5,213,898 | 5/1993 | Larm et al. | 428/422 |
| 5,217,492 | 6/1993 | Guire et al. | 623/11 |
| 5,219,926 | 6/1993 | Lindman et al. | 525/54.1 |
| 5,240,994 | 8/1993 | Brink et al. | 525/54.2 |
| 5,250,613 | 10/1993 | Bergstrom et al. | 525/54.1 |
| 5,258,041 | 11/1993 | Guire et al. | 623/66 |
| 5,308,641 | 5/1994 | Cahalan et al. | 427/2 |

FOREIGN PATENT DOCUMENTS

| | | |
|---|---|---|
| 1160548 | 1/1984 | Canada . |
| 0020193 | 12/1980 | European Pat. Off. . |
| 0295905B1 | 12/1988 | European Pat. Off. . |
| 276814A1 | 3/1990 | Germany . |
| 88/02623 | 4/1988 | WIPO . |
| 91/16932 | 11/1991 | WIPO . |
| WO92/00747 | 1/1992 | WIPO . |
| 92/07023 | 4/1992 | WIPO . |
| WO93/05793 | 4/1993 | WIPO . |
| WO93/05825 | 4/1993 | WIPO . |

OTHER PUBLICATIONS

Hoffman et al., "A New Method for Covalent Coupling of Heparin and Other Glycosaminoglycans to Substrates Containing Primary Amino Groups", *Carbohydrate Research*, 117 (1983) 328–331.

Larm et al., "A New Non–Thrombogenic Surface Prepared by Selective Covalent Binding of Heparin Via a Modified Reducing Terminal Residue", 1984.

Larm et al., "An Approach to Antithrombosis by Surface Modification", *Progress in Artificial Organs*, 1985, 313–318.

*Primary Examiner*—Nathan M. Nutter
*Attorney, Agent, or Firm*—Gary L. Griswold; Walter N. Kirn; Paul W. Busse

[57] ABSTRACT

A process for modifying a surface of an article that includes treating the surface with (a) a first water-soluble polyalkylene amine, (b) a water-soluble polymeric anionic compound, and (c) a second water-soluble polyalkylene amine in the absence of crosslinking agents to create a modified surface.

7 Claims, No Drawings

PROCESS FOR MODIFYING SURFACES

BACKGROUND OF THE INVENTION

This invention relates to modifying the surface of an article, e.g., to render that surface biocompatible.

Surfaces of, e.g., medical devices must often be modified in order to render the surfaces biocompatible. For example, the surfaces of medical devices that are in direct contact with blood or blood products (e.g., blood oxygenators, blood pumps, catheters, and tubing) have been treated with biologically active agents such as heparin or derivatives thereof to make such surfaces nonthrombogenic in an effort to prevent clotting or clot formation related to surface contact with blood or blood products.

One problem associated with such treatment is that the biologically active agent often does not remain fixed on the surface of the treated article. One solution to this problem has been to prime the surface using a combination of a polyalkylene amine and a crosslinking agent. While this treatment is generally effective, it necessitates the use of an additional chemical, namely, the crosslinking agent.

SUMMARY OF THE INVENTION

In one aspect, the invention features a process for modifying the surface of an article that includes treating the surface with (a) a first water-soluble polyalkylene amine, (b) a water-soluble polymeric compound, and (c) a second water-soluble polyalkylene amine, all in the absence of crosslinking agents, to create a modified surface.

In a second aspect, the invention features a process for modifying the surface of an article that includes (a) treating the surface with (i) a first water-soluble polyalkylene amine, (ii) a water-soluble polymeric anionic compound, and (iii) a second water-soluble polyalkylene amine, all in the absence of crosslinking agents, to cream a primed surface; and (b) contacting the primed surface with a biologically active agent to bind the biologically active agent to the primed surface.

In preferred embodiments, the modified or primed surface is essentially free of quaternary ammonium groups. Moreover, the surface of the article prior to treatment with the polyalkylene amines and polymeric anionic compound is preferably essentially free of surface oxidation. The primed surface is preferably contacted with the biologically active agent in the presence of a reducing agent to covalently bind the biologically active agent to the primed surface.

The polyalkylene amine preferably contains at least two primary amino groups in each polymer molecule. An example of a preferred polyalkylene amine is polyethylene imine. The polymeric anionic compound is preferably a polysaccharide such as dextran sulfate. The biologically active agent may be an anti-thrombotic agent (e.g., a glycosaminoglycan (or derivative thereof) such as heparin or a heparin derivative). Other examples of suitable biologically active agents include heparan sulfate, hyaluronic acid, dermatan sulfate, chitosan, and derivatives thereof.

The invention also features an article that includes a substrate having a biocompatible surface that includes (a) a primer that includes the reaction product of (i) a first water-soluble polyalkylene amine, (ii) a water-soluble polymeric anionic compound, and (iii) a second water-soluble polyalkylene amine; and (b) a biologically active agent bound to the primer. The primer is essentially free of crosslinking.

Throughout this application the following definitions apply:

A "biocompatible" surface is a surface which, when in contact with a patient's blood, plasma, or other body fluids, does not cause an adverse physiological reaction.

A "biologically active agent" is a material which, when in contact with a patient's blood, plasma, or other body fluids under physiological conditions, exhibits biological activity. For instance, a material such as heparin is "biologically active" in the sense that it acts as an anti-coagulant in the presence of blood.

A surface that is "essentially free of oxidation" refers to a surface that has not been pre-treated, e.g., by exposure to chemical oxidizing agents or a plasma, to cause oxidation of the surface. Thus, such a surface is essentially free of, e.g., carbonyl-containing and/or carboxyl-containing groups generated by such an oxidation process.

The invention provides a simple and effective means for modifying the surface of an article, e.g., to render that surface biocompatible. Surprisingly, the process is effective despite the fact that the priming operation is conducted in the absence of crosslinking agents.

Other features and advantages of the invention will be apparent from the following description of the preferred embodiments thereof, and from the claims.

DETAILED DESCRIPTION

The present invention provides a process for producing modified surfaces (e.g., the surfaces of medical devices such as tubes, catheters, oxygenators, filters, intravascular probes, blood pumps, blood gas sensing devices, and the like). The surface (which may be a hydrophobic or hydrophilic surface) need not be oxidized prior to treatment (e.g., by exposure to chemical oxidizing agents such as sulfuric acid and potassium permanganate, or to an $R_f$ plasma). Examples of suitable surfaces include polypropylene, polyvinyl chloride, polymethyl methacrylate, polytetrafluoroethylene, polysulfone, silicone rubber, polyethylene terephthalate, polycarbonate, polyethylene, polystyrene, and polyurethane.

In general, the surface is first contacted with a polyalkylene amine such as polyethylene imine to give a surface that is both wettable and positively charged. Next, a polymeric anionic compound such as dextran sulfate is added to the positively charged surface, thereby further increasing the wettability of the surface; examples of other suitable polymeric anionic compounds include polygalacturonic acid and polyacrylic acid. The use of a polymeric anionic compound also allows the addition of a second polyalkylene amine (which may be the same as, or different from, the first polyalkylene amine) to the surface, which follows application of the polymeric anionic compound. Thus, at this point, the surface has been sequentially treated with three agents to create a primed surface: (1) first polyalkylene amine, (2) polymeric anionic compound, and (3) second polyalkylene amine. Treatment is conducted in the absence of crosslinking agents. The sequence may be repeated as many times as necessary, the particular number of steps being selected by the particular application for which the treated article is intended.

The primed surface may then be contacted with a biologically active agent such as heparin, heparan sulfate, hyaluronic acid, dermatan sulfate, chitosan, or derivatives thereof to bind the biologically active agent to the primed surface. Binding may be either ionic or covalent, with covalent being preferred. Following addition of the biologically active agent, the biologically active agent may then be treated with a crosslinking agent, if desired. The underlying primer, however, remains uncrosslinked.

In the case of covalent binding, it is preferred to contact the primed surface with a biologically active agent having free aldehyde groups (generated, e.g., by periodate oxidation) in the presence of a reducing agent such as sodium cyanoborohydride which covalently binds the agent to the polyalkylene amine. The covalent binding of the biologically active agent to the polyalkylene amine most likely occurs when a reactive aldehyde group of the biologically active agent reacts with a primary amino group of the polyalkylene amine. The Schiffs' base initially formed as a result is readily reduced to a secondary amine in the presence of the sodium cyanoborohydride.

Covalent binding may also be accomplished using a carbodiimide coupling agent, rather than sodium cyanoborohydride, in which case it is not necessary to use biologically active agents having free aldehyde groups.

The invention will now be further described by way of the following non-limiting examples.

EXAMPLES

In the examples, the surface-bound concentration of heparin may be measured by a thrombin inhibition assay. The inhibition assay exploits the observation that thrombin enzymatically cleaves a synthetic substrate (S-2238) to yield a product whose concentration is proportional to its absorbance at 405 nm, and the concentration of product is therefore proportional to the thrombin concentration. Decreased amounts of product reflect inhibition of thrombin by heparin in the presence of excess amounts of antithrombin-III.

Briefly, the assay is performed by adding, in the following sequence, the following materials to test tubes: an unknown sample and 0.05 ml of buffer (where a sample has an unknown concentration of heparin on the surface), or 0.05 ml of a standard heparin solution; 1.0 ml of 0.3 mM S-2238; 0.1 ml of antithrombin-III (5 units/ml); and 0.1 ml of thrombin (0.1 units/ml). The standard heparin solutions (50 microliters) contain 0.08, 0.04, 0.02, 0.01, and 0.0 micrograms of heparin, respectively. The assay is carried out at 37° C. with overnight incubation in a water bath, with continuous mixing. Measurements are made on 0.20 ml aliquots taken from the unknown and standard solutions using microtiter plates, and optical density at 405 nm is recorded. The optical density values are related to heparin concentration using the standard heparin solutions.

More specifically, the assay procedure is a modification of Chandler et at., *J. Biomed. Mater. Res.*, 22:497–508 (1988) which uses the following reagents:

| Reagent | Manufacturer |
| --- | --- |
| Antithrombin-III | Sigma |
| S-2238 | Kabi |
| Thrombin | Sigma |
| Hanks' Buffer | Sigma |
| Heparin | Sigma |

Antithrombin-III is reconstituted to 5 units/ml with 10 ml deionized distilled water and refrigerated at 4° C. S-2238 is reconstituted to 0.3 mM using 133 ml of a buffer stock solution of PBS (phosphate buffered saline) with 1 mg/ml BSA (bovine serum albumin, Cat. No. A7838, Sigma Chemical Company, St. Louis, Mo.), and 1 mg/ml polyethylene glycol (8000 MW, Cat. No. P2139, Sigma Chemical Company, St. Louis, Mo.), and stored at 4° C. Thrombin is reconstituted to 10 units/ml Hanks' phosphate buffered saline, and stored at −20° C. in 1 ml aliquots. A 1:100 dilution of thrombin is used in the assay.

Standard heparin solutions are prepared from the 10 units/ml stock solution by serial dilution. Each new batch of thrombin and/or heparin must be tested to ensure maximum sensitivity. Representative values of standard heparin solutions are listed in the following table.

| Standards | Concentration |
| --- | --- |
| 1 | 0.08 µg/50 µl |
| 2 | 0.04 µg/50 µl |
| 3 | 0.02 µg/50 µl |
| 4 | 0.01 µg/50 µl |
| 5 | 0 µg/50 µl |

To measure absorbance, 0.05 ml of each of the appropriate standards, as well as an unknown sample having a measured surface area, together with PBS/BSA buffer (0.05 ml) are dispensed into tubes. The following reagents are then added to each of the tubes: 0.1 ml antithrombin-III, 1.0 ml S-2238, and 0.1 ml thrombin. All tubes are then vortexed and incubated overnight at 37° C. After incubation, 0.2 ml from each tube is added to a well of a microliter plate in duplicate for each tube, and optical density readings are taken at 405 nm. All standards and samples are run in duplicate, with duplicate optical density readings at 405 nm.

Example 1

Various samples listed in Table I were treated by first immersing the sample in a 0.1% by weight aqueous solution of polyethylene imine (PEI, average molecular weight 50,000, Aldrich Chemical Co., Milwaukee, Wis.) for 15 minutes at room temperature. The sample was then rinsed thoroughly in water, and then immersed for 5 minutes at room temperature in a 0.03% by weight solution of dextran sulfate (average molecular weight 500,000, Sigma Chemical Co., St. Louis, Mo.) in citrate buffer (11.0 g citric acid monohydrate and 9.0 g sodium chloride in one liter of water, adjusted to pH 3.9 with 5N sodium hydroxide).

Following dextran sulfate treatment, the sample was rinsed thoroughly with water and then immersed again in the aqueous PEI solution for 15 minutes at room temperature. Following a thorough rinsing with water, the sample was immersed in a solution containing 0.04% by weight periodate oxidized heparin and 0.004% by weight sodium cyanoborohydride (Aldrich Chemical Co., Milwaukee, Wis.) in the above-described titrate buffer for 2 hours at 50° C.

Periodate oxidized heparin was prepared by dissolving 15 g sodium heparin (Diosynth Inc., Chicago, Ill.) and 1.5 g sodium periodate in 450 ml of phosphate buffered saline (pH 7), and then stirring the solution in the dark for one hour. 15 g of glycerin was then added to quench the unreacted periodate, after which the mixture was stirred for one hour and then dialyzed against water (4 times, using a total of 4 liters of water) using 3500 MWCO dialysis tubing. The dialyzed solution was then lyophilized to yield 8 g of periodate oxidized heparin.

Following exposure to the periodate oxidized heparin/sodium cyanoborohydride solution, the sample was rinsed thoroughly with water and then with 25% saline for 5 minutes at room temperature, followed by a final water rinse. Each sample was then tested for heparin activity using the thrombin inhibition assay (described above). The results (in $\mu g/cm^2$) are shown in Table I. In addition, the presence of heparin on all surfaces was confirmed by staining with toluidine blue.

TABLE I

| SAMPLE | HEPARIN ACTIVITY | |
| --- | --- | --- |
| | Heparinized ($\mu g/cm^2$) | Not Heparinized |
| PMMA | 0.05 | none |
| Polytetrafluoroethylene | 0.06 | none |
| Polysulfone | 0.06 | none |
| Silicone Rubber | 0.06 | none |
| PET | 0.08 | none |
| Polypropylene | 0.10 | none |
| Polycarbonate | 0.07 | none |

The samples used in Table I were the following:

PMMA: Polymethyl methacrylate available as "PLEXIGLASS" from Rohm and Haas of Philadelphia, Pa.;

Polytetrafluoroethylene: available as "TEFLON" from Zeus Industrial Products, Inc. of Raritan, N.J.; Polysulfone: available as "THERMALUX" from The Westlake Companies of Reading, Pa.

Silicone rubber: available as "SILASTIC" from Dow Corning of Midland, Mich.;

PET: Polyethylene terephthalate available as "SCOTCHPAR" from 3M Company of St. Paul, Minn.;

Polypropylene: porous polypropylene available as "CELGARD" from Hoechst Celanese of Charlotte, N.C.;

Polycarbonate: available as "HYZOD" from Sheffield Plastics Inc. of Sheffield, Mass.

The thrombin inhibition assay could not be used accurately to test materials such as polyvinyl chloride and polyurethane because these materials absorb some of the chromophore liberated during the assay. The presence of heparin on these surfaces, however, was confirmed by staining with toluidine blue.

Example 2

The procedure according to Example 1 was followed using, as the substrate, a polycarbonate sample ("HYZOD" available from Sheffield Plastics Inc. of Sheffield, Mass.) except that the sample was immersed in the solution containing 0.04% by weight periodate oxidized heparin and 0.004% by weight sodium cyanoborohydride (Aldrich Chemical Co., Milwaukee, Wis.) in citrate buffer for 30 minutes at 50° C., rather than 2 hours.

Example 3

Two Sarns/3M oxygenators (made of polypropylene, polycarbonate, and stainless steel, Model Turbo 440, Sarns/3M, Ann Arbor, Mich.), as well as the related centrifugal pumps (made of polycarbonate and polymethyl methacrylate), cannulae, reservoir bags, and tubing (all made of polyvinyl chloride) were treated according to the procedure of Example 2 to modify the blood contacting surfaces of each part of each system. Following treatment, each system was rinsed thoroughly with phosphate buffered saline (pH 7).

Qualitative blood compatibility was tested in pigs using a partial heart-bypass procedure. With nonsystemic heparin, blood flow was maintained through each treated system for a period of 3 hours at a flow rate of 2 to 2.5 liters/min.

At the end of the 3 hour period, each system was disassembled and visually examined for the presence of thrombi. In each case, the oxygenator fiber bundle was virtually thrombus free, although there were occasional small thrombi on a stainless steel heat exchanger. For comparative purposes, a similar bypass experiment was run using a circuit in which the oxygenator was not heparinized. In this experiment, occasional thrombi were seen on the fiber bundle and substantial thrombus formation was seen on the heat exchanger.

Other embodiments are within the following claims.
What is claimed is:

1. A process for modifying a surface of an article comprising treating said surface with (a) a first water-soluble polyalkylene amine, (b) a water-soluble polymeric anionic compound, and (c) a second water-soluble polyalkylene amine in the absence of crosslinking agents to create a modified surface.

2. The process of claim 1 wherein at least one of said polyalkylene amines contains at least two primary amino groups in each polymer molecule.

3. The process of claim 1 wherein at least one of said polyalkylene amines comprises polyethylene imine.

4. The process of claim 1 wherein said polymeric anionic compound comprises a polysaccharide.

5. The process of claim 1 wherein said polymeric anionic compound comprises dextran sulfate.

6. The process of claim 1 wherein said modified surface is essentially free of quaternary ammonium groups.

7. The process of claim 1 wherein said surface is essentially free of oxidation prior to treatment with said polyalkylene amines and said polymeric anionic compound.

* * * * *

UNITED STATES PATENT AND TRADEMARK OFFICE
CERTIFICATE OF CORRECTION

PATENT NO.: 5,532,311

DATED: July 2, 1996

INVENTOR(S): Larry M. Sirvio and Barbara C. Swenson

It is certified that error appears in the above-identified patent and that said Letters Patent is hereby corrected as shown below:

Column 4, line 56    "titrate" should read --citrate--

Signed and Sealed this

Seventh Day of January, 1997

Attest:

BRUCE LEHMAN

Attesting Officer        Commissioner of Patents and Trademarks